US006901160B2

(12) United States Patent
Chapman et al.

(10) Patent No.: US 6,901,160 B2
(45) Date of Patent: May 31, 2005

(54) DIRECTIONAL LIGHTING AND METHOD TO DISTINGUISH THREE DIMENSIONAL INFORMATION

(75) Inventors: Kenneth Chapman, Sherwood, OR (US); Sam Dahan, Portland, OR (US)

(73) Assignee: Electro Scientific Industries, Portland, OR (US)

(*) Notice: Subject to any disclaimer, the term of this patent is extended or adjusted under 35 U.S.C. 154(b) by 714 days.

(21) Appl. No.: 09/842,436

(22) Filed: Apr. 26, 2001

(65) Prior Publication Data

US 2002/0009218 A1 Jan. 24, 2002

Related U.S. Application Data

(60) Provisional application No. 60/200,776, filed on Apr. 28, 2000.

(51) Int. Cl.[7] .................................................. G06K 9/00

(52) U.S. Cl. ....................... 382/141; 382/154; 382/190; 348/126; 348/131; 348/208.8; 356/237.4

(58) Field of Search ................................ 382/141, 151, 382/145, 147, 154, 173, 190, 308; 205/559.04, 559.19, 559.12, 559.29, 208.1, 559.46, 559.32, 559.08, 559.07, 559.05; 348/87, 126, 131, 132, 151, 208.8; 356/237.4, 237.2

(56) References Cited

U.S. PATENT DOCUMENTS 5,608,547 A 3/1997 Nakatani et al. ............ 358/505
5,774,574 A * 6/1998 Hoki .......................... 382/149
5,859,698 A * 1/1999 Chau et al. .............. 356/237.2
5,920,387 A * 7/1999 Nakajo et al. ........... 356/237.4
5,943,125 A * 8/1999 King et al. .............. 356/237.1
5,949,901 A * 9/1999 Nichani et al. ............. 382/149
6,177,682 B1 * 1/2001 Bartulovic et al. .... 250/559.44
6,256,088 B1 * 7/2001 Gordon ....................... 356/73
6,353,222 B1 * 3/2002 Dotan ........................ 250/310
6,658,144 B1 * 12/2003 Hatab ......................... 382/144

FOREIGN PATENT DOCUMENTS

DE 19511534 10/1996
EP 0 898 163 A 2/1999
EP 1 030 173 A 8/2000
JP 63215952 8/1988
JP 04279848 5/1992

OTHER PUBLICATIONS

PCT International Search Report (Application No. PCT/US 01/13477).

* cited by examiner

*Primary Examiner*—Bhavesh M. Mehta
*Assistant Examiner*—Sheela Chawan
(74) *Attorney, Agent, or Firm*—Young & Basile, P.C.

(57) ABSTRACT

The present invention provides a method and an apparatus for evaluating the surfaces of substrates for three dimensional defects. The present invention uses low-angled lighting positioned on opposite sides of the substrate. A camera positioned above the substrate captures two images thereof, one using the first light source and one using the second. The first and second images are subtracted from one another to create a third image. Camera data suggestive of three dimensional features is emphasized by subtracting the two images and can be evaluated. A fourth image may be created by selecting the minimum values between the first and second images on a point-by-point basis. The fourth image also provides useful information in evaluating three dimensional defects.

24 Claims, 5 Drawing Sheets

DIRECTIONAL LIGHTING AND METHOD TO DISTINGUISH THREE DIMENSIONAL INFORMATION

CO-PENDING APPLICATION

This application claims the benefit of the priority date of co-pending Provisional Application Ser. No. 60/200,776, filed Apr. 28, 2000 in the names of Kenneth Chapman and Sam Duhan, the entire contents of which is incorporated herein by reference.

FIELD OF THE INVENTION

The present invention relates to inspecting the surface of surface-mounted components for three-dimensional data.

BACKGROUND OF THE INVENTION

Surface-mounted components are inspected at many stages of their manufacture and for many different flaws. One type of component is a surface-mounted multi-layered ceramic capacitor (MLCC) component. As they are manufactured and used these components must be smooth, or planar. These components are typically made from ceramic and thus can be comparatively easily scratched, chipped or broken. These types of defects are generally referred to as three-dimensional, or 3-D defects. Ceramic components may also include other types of 3-D defects such as holes.

A core problem with inspecting ceramic components for 3-D defects is that it is difficult to distinguish between an unacceptable 3-D defect and an acceptable stain. To solve this problem the prior art developed highly sophisticated vision algorithms. Because a certain amount of imperfection can be tolerated, the algorithms must also qualify the 3-D defects as to whether they compel the rejection of a component or whether they can be tolerated. These algorithms did not operate as quickly as many manufacturers would have liked because of the amount of computer processor time they required. Further, the prior art algorithms required that the components move at a comparatively slow rate so that the inspection could be carried out. The prior art techniques often resulted in an artificially high rejection rate as vision algorithms could not distinguish between discolorations and 3-D defects.

Therefore a need has arisen to provide an inspection system that can easily distinguish 3-D information from 2-D information at a comparatively faster rate without the use of excessive computational power.

SUMMARY OF THE INVENTION

The present invention provides a method and apparatus for cost effectively evaluating three-dimensional features on a substrate.

One aspect of the method of the present invention provides for evaluating three-dimensional features on a substrate including illuminating the substrate from a first angle and capturing a first image of the substrate. The first image is made up of a plurality of pixels, the pixels having an address and a value. The pixel address corresponds to a location on the substrate. The method also provides for illuminating the substrate from a second angle and capturing a second image of the substrate. The second image is also made up of a plurality of pixels where the pixels are addressed in the same manner as the pixels in the first image. Each pixel in the second image also has a value. The pixel values from the first image are subtracted from the pixel values in the second image on a pixel address by pixel address basis to create a third image. The third image is processed to determine the quantity of pixels characteristic of three-dimensional features therein. The substrate is rejected if the quantity pixels characteristic of three-dimensional features exceeds a predetermined value.

A further aspect of the method of the present invention involves applying a threshold to the third image such that the pixel values are either zero or above the threshold. The non-zero pixel values are characteristic of three-dimensional features on the substrate. The pixel addresses corresponding to the non-zero pixel values may then be recorded. The method may provide for creation of a fourth image by selecting the minimum pixel value between the first and second images on a pixel address by pixel address basis. Then the fourth image may be processed at the recorded pixel addresses to evaluate the pixel values at the recorded locations. The substrate may be rejected if the evaluation of the pixel values is outside defined tolerances.

Another aspect of the present invention provides an apparatus for evaluating three-dimensional features on a surface of a substrate. The apparatus includes a first light source positioned at a low angle relative to the substrate such that when the first light source illuminates the surface of the substrate, three-dimensional features on the surface of the substrate, having a first orientation, produce glints. A second light source is provided where the second light source is positioned opposite from the first light source such that when the second light source illuminates the surface of the substrate, three-dimensional features on the surface of the substrate, having a second orientation, produce glints. A camera is positioned perpendicularly above the substrate and the camera captures images of the substrate. The images are made up of a plurality of pixels, the pixels including an address characteristic of a location on the surface of the substrate and a value. The camera captures a first image of the substrate when the substrate is illuminated by the first light source, and the camera captures a second image of the substrate when the substrate is illuminated by the second light source. A processor is provided where the processor is configured to calculate the difference between the pixel values in the first image and the pixel values in the second image on a pixel address-by-pixel address basis to form a third image. The processor is further configured to count the number of pixel addresses in the third image that are characteristic of three-dimensional features.

According to a further aspect of the apparatus of the present invention, the processor applies a threshold to the third image such that the pixel values in the third image are either zero or above the threshold. The pixel values that exceed the threshold are characteristic of three-dimensional features. The processor is operative in counting the non-zero values within the third image and indicating that the substrate is rejected if the number of non-zero pixel values exceeds a predetermined value.

According to a further aspect of the apparatus of the present invention the processor records the pixel addresses of those pixel values in the in the third image that exceed the threshold. The processor then selects the minimum pixel value between the first and second images on a pixel address basis to create a fourth image. The processor is configured to evaluate the pixel values in the fourth image at and around the recorded locations. The processor rejects the substrate if the evaluation of the pixel values at and around the recorded addresses fall outside defined tolerances.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views and wherein.

DESCRIPTION OF THE PREFERRED EMBODIMENT

The present invention uses directional lighting to highlight 3-D regions in an image. In particular, the present invention captures two images of a substrate, typically made from ceramic, with low-angled lighting positioned at opposite ends of the component. The images are subtracted from one another such that the 3-D regions on the component are identified. The 3-D regions are found in the subtracted image to further evaluate the 3-D regions.

Additionally, the system may record the locations at which the recorded locations may be used to process a minimum image when the minimum image is made up of the minimum values between the two captured images. The substrate may be rejected based on the salvation of the minimum image.

Figure 1:
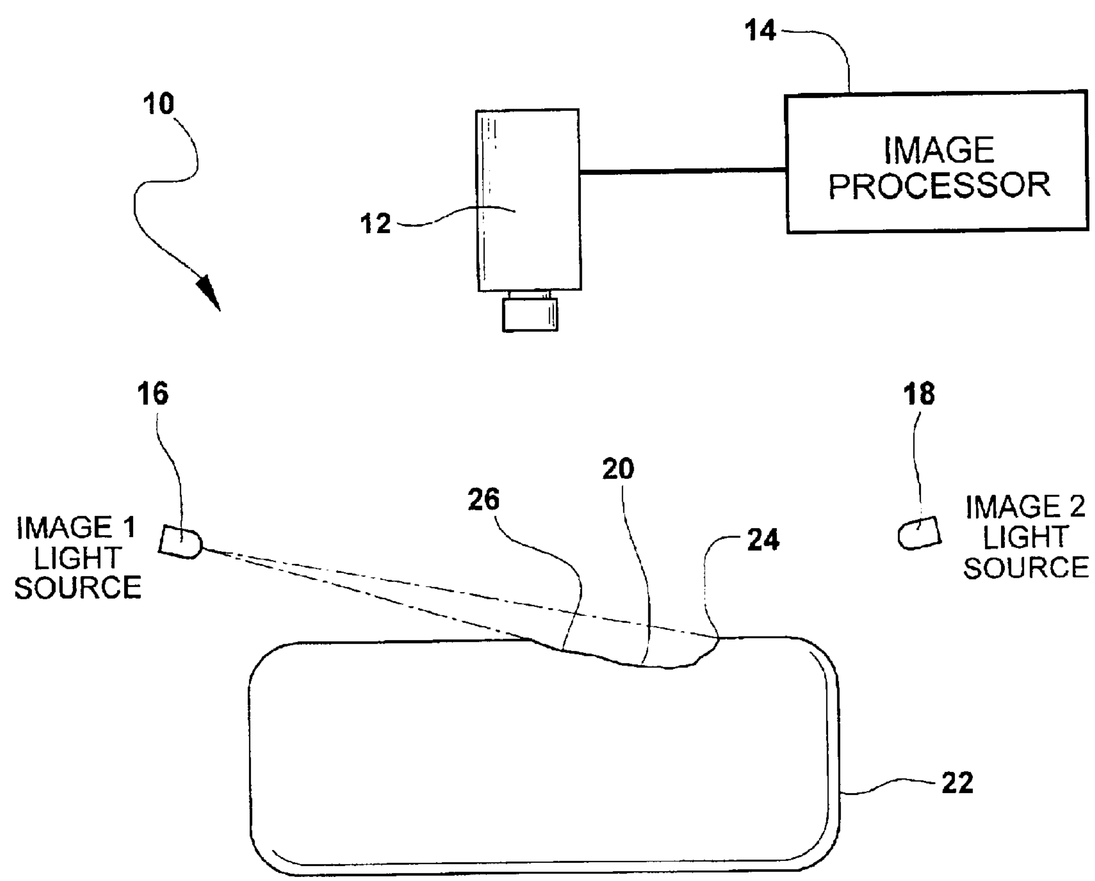
FIG. 1 is a schematic representation of the vision system of the present invention.

With reference to the figures and in particular to FIG. 1, there is shown a vision system 10. Substrate 22 is typically ceramic, but it is understood that the present invention is not limited to the inspection of any particular substrate. Typically vision systems inspect components fairly comprehensively. That is, as described in the background of the invention, they inspect components for overall size, etc. Such inspection may also include measurement of the length of the termination band. The present invention is directed to 3-D features or defects including but not limited to scratches and cracks.

The vision system 10 includes a camera 12 positioned perpendicularly above a substrate 22. Camera 12 preferably captures an eight-bit gray-scale image having 256 different shades of gray, valued between 0 and 255. The images output from camera 12 are made up of a pixels. Each pixel has an address and a value. The address of the pixel is characteristic of a location on the surface of the substrate. The value of a pixel is the gray-scale value. In the preferred embodiment a CCD camera is used having an array of 640×480 pixels which is available for purchase from Opteon. It is recognized that any other type of digital camera may be used, such as a CMOS sensor. Data from camera 12, which represents an image of the substrate 22, is output to an image processor 14. Image processor 14 processes the data as described below to accept or reject the component based on evaluation of pixel data characteristic of the 3-D factors. The image processor 14 preferably is a personal computer (PC).

In the first preferred embodiment, two light sources 16 and 18 are positioned at opposite ends of substrate 22. In the preferred embodiment, light sources 16 and 18 are LED illuminators that can be controlled quickly such that each one illuminates sequentially. LED illumination is preferred because it is a rapid illumination technique, but it is not monochromatic such that it creates interference effects. It is understood that other type of quick illumination could be used such as strobe illumination.

Figure 2:
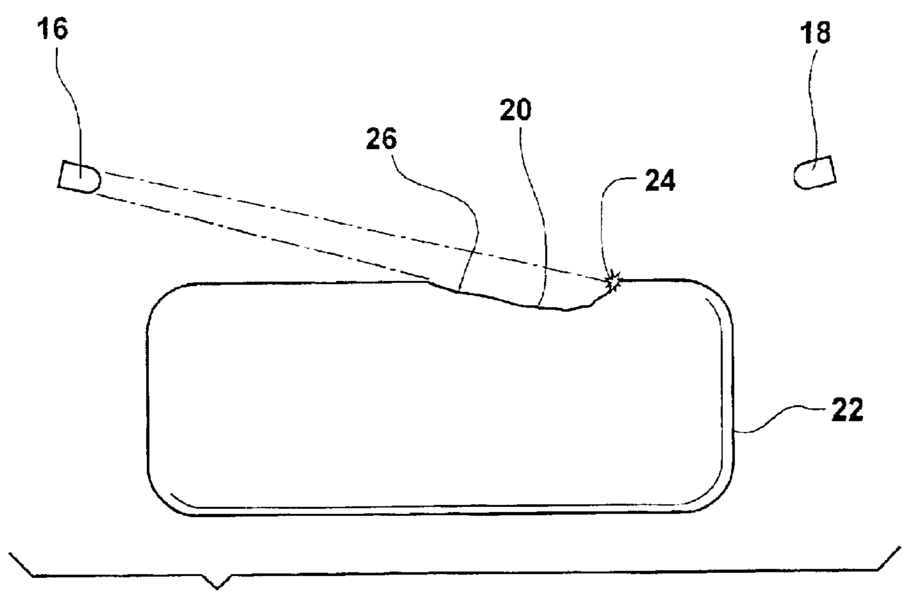
FIG. 2 illustrates the present invention using a first light source.
Figure 2A:
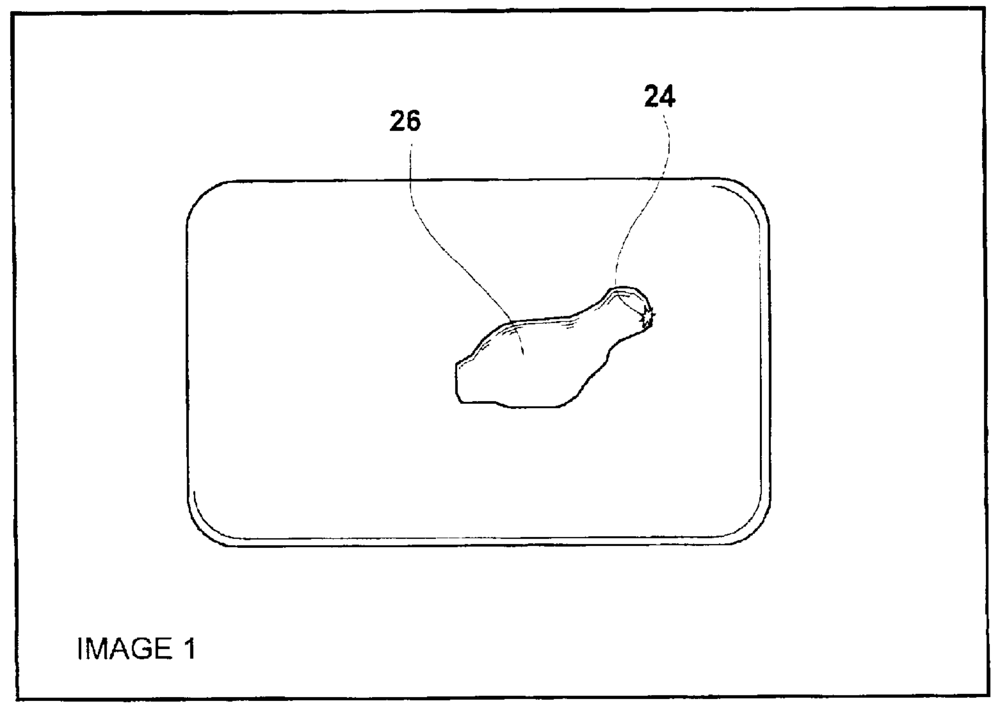
FIG. 2A is an image captured using the first light source.
Figure 3:
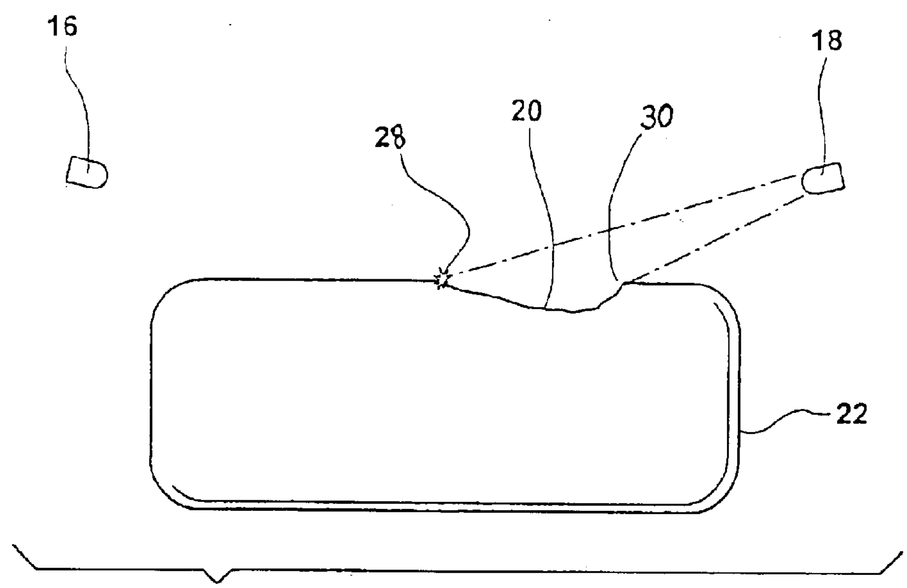
FIG. 3 illustrates the present invention using a second light source.
Figure 3A:
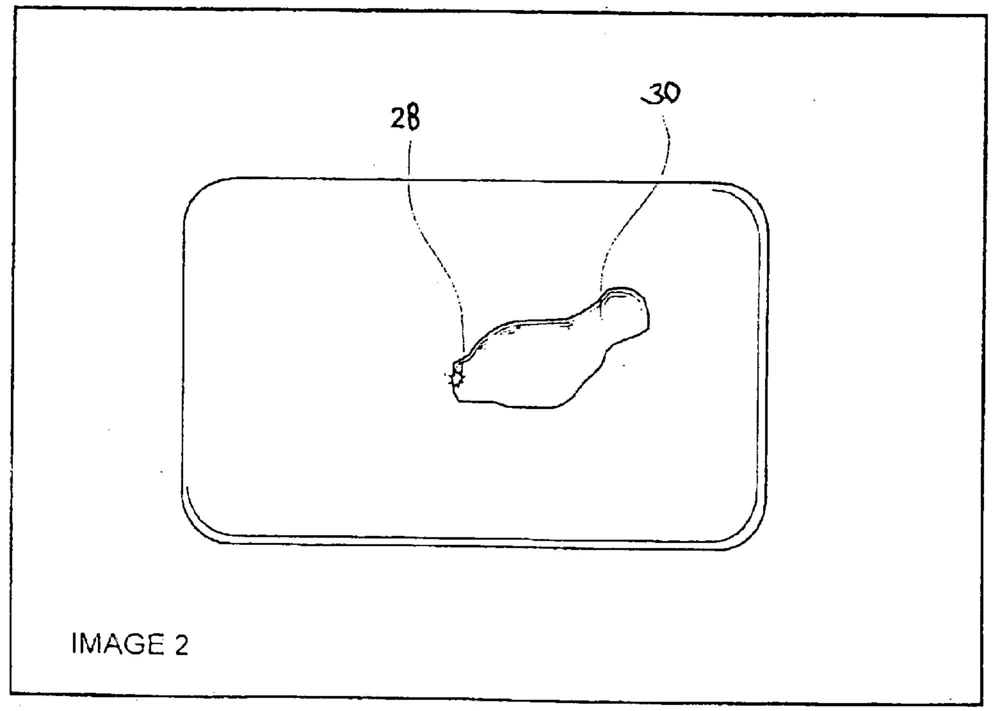
FIG. 3A is an image captured using the second light source.
Figure 6:
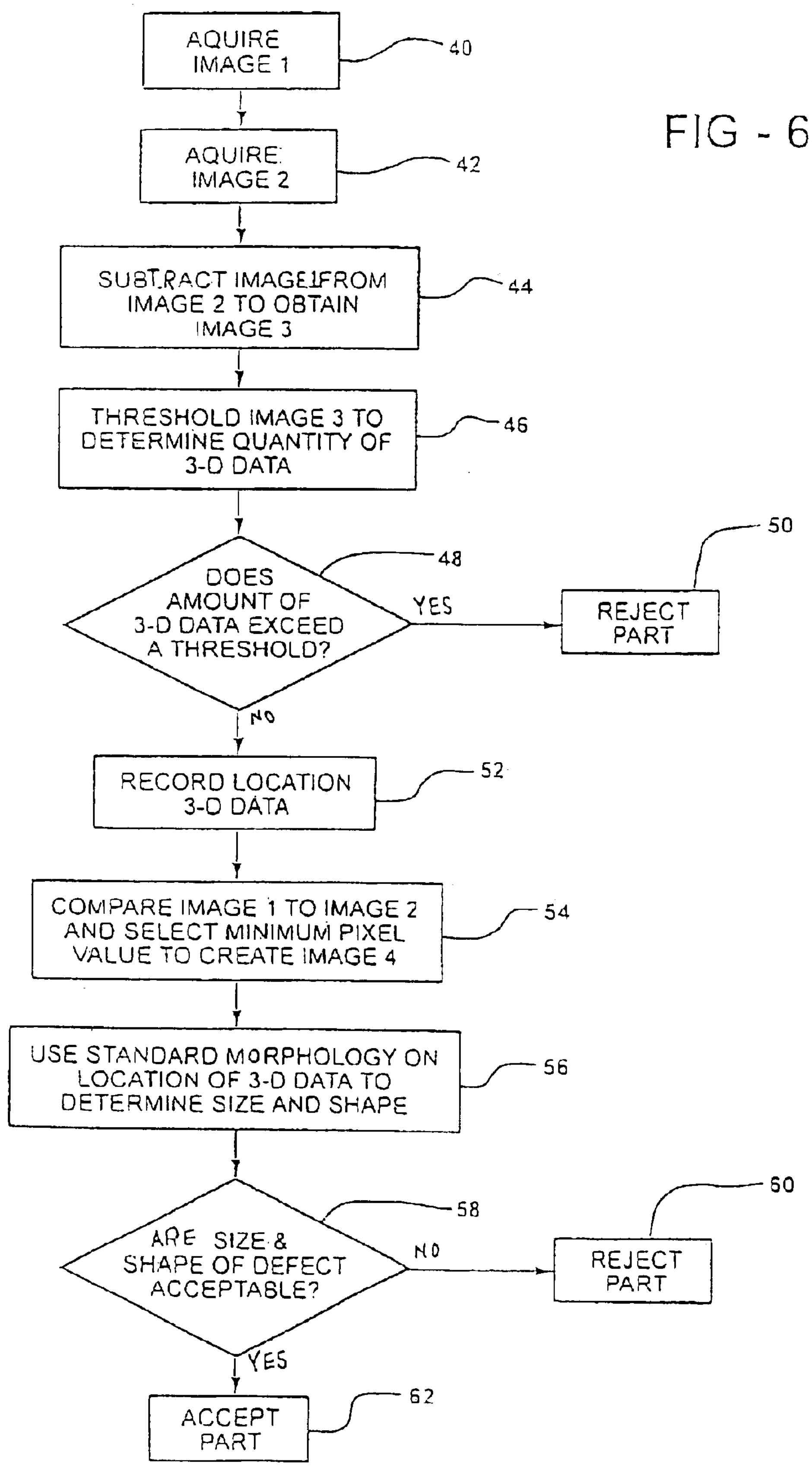
FIG. 6 is a flow chart illustrating the process of the present invention.

With reference to FIGS. 2 and 3, as well at the flow chart illustrated at FIG. 6 vision system 10 captures two distinct images of substrate 22, at 40 and 42. Each image is captured by camera 12. As shown in FIGS. 2 and 2A the first image, or IMAGE 1 is captured using illumination from light source 16. Similarly as shown in FIGS. 3 and 3A and the second image, or IMAGE 2 is captured using illumination from light source 18. As shown in FIGS. 1 and 2, when IMAGE 1 is captured with light source 16, a 3-D feature 20 will produce a glint 24 on the side of the feature 20 distal from light source 16, and the feature 20 will produce a shadow 26 on the side of defect 20 proximate to light 16. As captured by camera 12 and illustrated by FIG. 2A, glint 24 will result in locally higher gray-scale values, and shadow 26 will result in locally lower gray-scale values. In the typical case, glint 24 will result in enough light to result in a gray-scale value of 255. IMAGE 1, as captured by camera 12 includes a plurality of pixels where the pixels have an address and a value. The address is characteristic of a location on the substrate.

As illustrated in FIGS. 3 and 3A IMAGE 2 is captured using illumination from light source 18. As captured with light source 18, a glint 28 appears where the shadow 26 had been in IMAGE 1 and a shadow 30 appears where the glint 24 had been. FIG. 3A represents IMAGE 2. IMAGE 2 is made up of the same number of pixels as IMAGE 1 and includes the same address scheme although IMAGE 2 includes different pixel values compared to IMAGE 1.

As shown in FIGS. 1, 2 and 3, light sources 16 and 18 are positioned at a low angle relative to substrate 22. It is understood by those of ordinary skill in the art that a smaller angle from the horizon will yield more 3-D data (as described below). However, as the angle from the horizon decreases the resulting images will be dimmer. It is also understood that as the light source is positioned at a higher angle from the horizon the image is brighter but the amount of 3-D data (as described below) decreases. It has been discovered that the preferred angle is between about ten degrees and fifteen degrees from the horizon. Positioning the light sources at this angle results in the optimum creation of glints and shadows for a wide range of 3-D defects.

Figure 4:
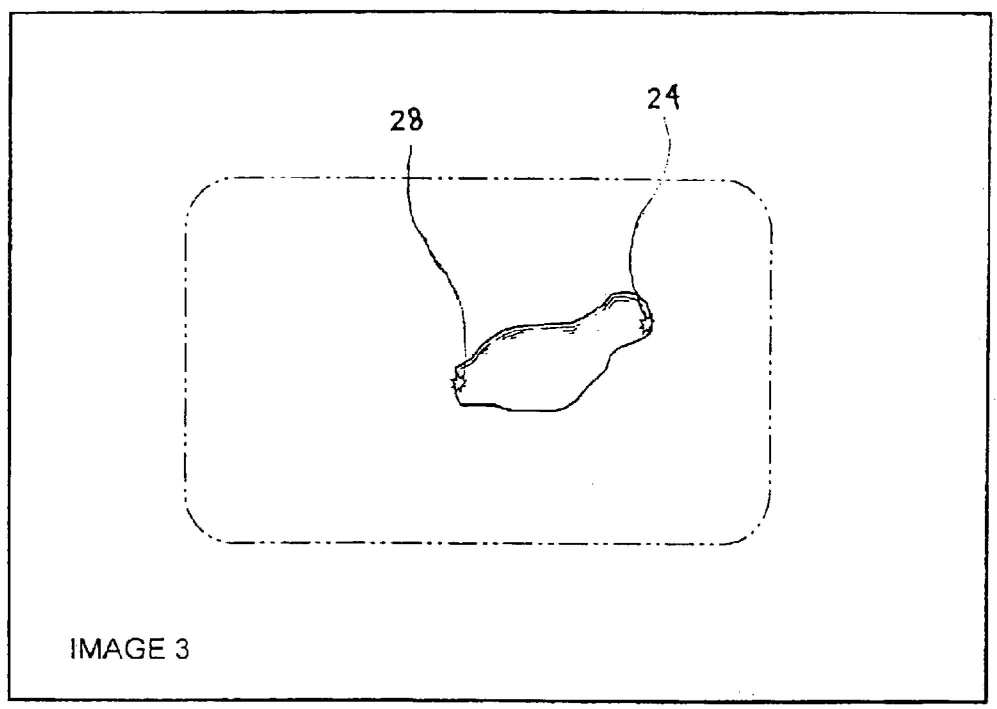
FIG. 4 is a third image created by taking the absolute value between FIGS. 2A and 3A.

With reference to FIG. 6 there is shown a flow chart describing, in its majority, the operation of image processor 14. As shown, IMAGE 1 and IMAGE 2 are captured at 40 and 42. As shown at 44 the pixel values from IMAGE 1 are subtracted from the pixel values from IMAGE 2 on a pixel address-by-pixel address basis. Thus, for 3-D data, glints are subtracted from shadows and shadows are subtracted from glints, each resulting in a comparatively high or bright value. For 2-D data the pixel values for any given pixel location in either of IMAGE 1 or IMAGE 2 will be the same, not close to the same. Thus, subtracting IMAGE 1 from IMAGE 2 for 2-D data will result in values of zero, or not much greater. IMAGE 3 is created as the absolute value between the difference between IMAGE 1 and IMAGE 2. FIG. 4 illustrates the absolute value between the difference between IMAGE 1 and IMAGE 2 where the background is black, and both glints are illustrated.

As shown at 46, image processor 14 applies a threshold to IMAGE 3 to eliminate artifacts. Thresholding an image is well known in the image processing field. Application of a threshold will yield pixel values that are zero or above the threshold. After a threshold has been applied to IMAGE 3, the image processor 14 can determine the magnitude of 3-D data by simply counting the number of pixel locations that have a non-zero value. If the number of pixel locations having a non-zero value exceeds another threshold at 48, the part is rejected as having an excess of 3-D data at 50. For purposes of the comparison at 48 the quality, or shape, of the 3-D defects is not evaluated. The threshold at 48 is based on the simple premise that if there is an excess of 3-D data at least some of that data must represent fatal defects. Preferably this threshold is set by a user when the system is initially installed based on the user's individual requirements.

Figure 5:
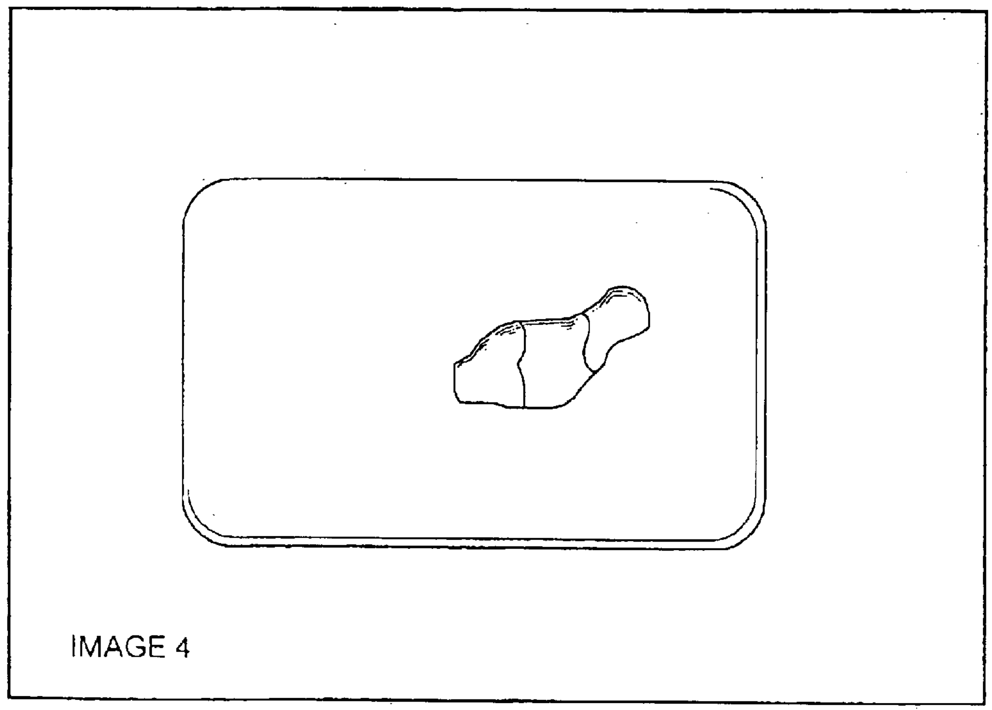
FIG. 5 is a fourth image created by taking the minimum value between FIGS. 2A and 3A.

If the amount of 3-D data is not so great as to warrant rejecting the component at 48 and 50, the system records the addresses at which the non-zero pixel values are located at 52. IMAGE 4 is created at 54. IMAGE 4 is created by comparing IMAGE 1 to IMAGE 2 and selecting the minimum pixel value for any given pixel address. This results in selecting the values representing the shadows as found in 3-D data from IMAGES 1 and 2. IMAGE 4 is illustrated at FIG. 5.

At 56, the image processor 14 processes IMAGE 4 at and around those locations containing 3-D data as recorded at 52, i.e., at and around the pixel addresses recorded at 52. Because the locations of the 3-D features are known based on recordation at 58, the image processor 14 can use standard morphology as recognized by those of skill in the art to access the shape and size of the 3-D feature. Such well-known techniques include gray-scale morphology. If the size and shape of the defect is acceptable, as defined by user set tolerances, the part is accepted relative to 3-D defects at 62; if the size and shape is unacceptable then the component is discarded at 60.

Morphology is used to eliminate any very small regions, leaving only those areas that are of a size large enough to be considered a defect. If the region is a 3-D region and it is large enough then it is a defect even if the total 3-D pixel count is not large enough to trigger rejection at 50. This may be the case where the morphology determines that the 3-D data is highly concentrated in a single area on the component. The morphology examines both the size of any individual 3-D defect (defined as a substantially contiguous area of 3-D data) as well as their concentration within a specific area. The basis for rejecting or accepting a component after determination of the size of the 3-D defect will depend on the specific component inspected as recognized by those of ordinary skill in the art.

The present invention allows components which include 3-D data below the initial threshold to be accepted as long as the contiguous regions of 3-D data are individually small.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for evaluating three dimensional features on a substrate comprising:

illuminating the substrate from a first angle and capturing a first image of the substrate, the first image comprising a plurality of pixels, the pixels having an address, and a value, the address corresponding to a location on the substrate;

illuminating the substrate from a second angle and capturing a second image of the substrate, the second image comprising a plurality of pixels, the pixels of the second image being addressed in the same manner as the pixels in the first image, and each pixel having a value;

subtracting the pixel values from the first image from the pixel values in the second image on a pixel address by pixel address basis to create a third image; and processing the third image to determine the quantity of pixels characteristic of three dimensional features therein and rejecting the substrate if the quantity of pixels characteristic of three dimensional features exceeds a predetermined value.

2. A method for evaluating a substrate as in claim 1 wherein a threshold is applied to the third image such that the pixel values are either zero or above the threshold, such that the values above the threshold are characteristic of three dimensional features on the substrate, the threshold being applied prior to processing the third image to determine the quantity pixels of characteristic three dimensional features.

3. A method for evaluating a substrate as in claim 2 wherein the threshold is set by a user.

4. A method as in claim 2 wherein the quantity of pixels characteristic of three dimensional data is determined by counting the pixel values which exceed the threshold.

5. A method as in claim 2 wherein the pixel addresses of all pixels in the third image which are above the threshold are recorded.

6. A method for evaluating a substrate as in claim 5 further comprising:

selecting the minimum pixel value between the first and second images on a pixel address by pixel address basis to create a fourth image; and processing the fourth image, at and around the recorded pixel addresses, and rejecting the substrate if the processing falls outside predetermined tolerances.

7. A method as in claim 6 wherein the fourth image is processed with gray scale morphology.

8. A method for evaluating a substrate as in claim 7 wherein the substrate is ceramic.

9. A method as in claim 1 wherein the first and second images are captured by a single camera positioned perpendicularly above the substrate.

10. A method as in claim 9 wherein the first angle is between 10 degrees and 15 degrees from the horizon and the second angle is between 170 degrees and 165 degrees from the horizon.

11. A method as in claim 9 wherein the three dimensional feature is manifested as a glint.

12. A method as in claim 1 wherein the subtracting step further comprises subtracting the pixel values from the first image from the pixel values in the second image on a pixel address by pixel address basis and using an absolute value of each resulting pixel value to create the third image.

13. An apparatus for evaluating three dimensional features on a surface of a substrate, the apparatus comprising:

a first light source positioned at a low angle relative to the substrate such that when the first light source illuminates the surface of the substrate three dimensional features on the surface of the substrate, having a first orientation, produce glints;

a second light source positioned opposite from the first light source, such that when the second light source illuminates the surface of the substrate, three dimensional feature-on the surface of the substrate, having a second orientation, produce glints;

a camera positioned perpendicularly above the substrate, the camera operative in capturing images of the substrate wherein the images are made up of a plurality of pixels, the pixels including an address characteristic of a location on the surface of the substrate and a value, the camera operative in capturing a first image of the substrate when the substrate is illuminated by the first light source and a second image of the substrate when the substrate is illuminated by the second light source; and a processor configured to calculate the difference between the pixel values in the first image and the second image on a pixel address by pixel address basis to form a third image; the processor further configured to calculate the number of pixel addresses in the third image which are characteristic of three dimensional features.

14. An apparatus as in claim 13 wherein the processor applies a threshold to the third image such that the pixel values in the third image are either zero or above the threshold, the non-zero pixel values being characteristic of three dimensional features, the processor operative in counting the non-zero values within the third image and indicating that the substrate is rejected if the number of non-zero pixel values exceed a predetermined value.

15. An apparatus as in claim 14 wherein the processor records the pixel addresses of the non-zero pixel values in the third image.

16. An apparatus as in claim 15 wherein the processor selects the minimum pixel value between the first and second images on a pixel address basis to create a fourth image, the processor configured to evaluate the size and concentration of the pixel values at the recorded locations, within the fourth image; the processor indicating that the substrate is rejected if the size and concentration of the three dimensional data exceeds predetermined tolerances.

17. An apparatus as in claim 16 wherein the processor utilizes gray scale morphology to determine the size and concentration of the three dimensional features within the fourth image.

18. An apparatus as in claim 13 wherein the first light source is positioned at an angle of approximately between 10 degrees and 15 degrees from the horizon.

19. An apparatus as in claim 18 wherein the camera is a CMOS camera.

20. An apparatus as in claim 13 wherein the processor is further configured to calculate the difference between the pixel values in the first image and the second image on a pixel address by pixel address basis and to take an absolute value of the difference on a pixel address by pixel address basis to form the third image.

21. An apparatus for evaluating three dimensional features on a surface of a substrate, the apparatus comprising:

a first light source positioned at a low angle relative to the substrate such that when the first light source illuminates the surface of the substrate three dimensional features on the surface of the substrate, having a first orientation, produce glints;

a second light source positioned opposite from the first light source, such that when the second light source illuminates the surface of the substrate, three dimensional features on the surface of the substrate, having a second orientation, produce glints;

a camera positioned perpendicularly above the substrate, the camera operative in capturing images of the substrate wherein the images are made up of a plurality of pixels, the pixels including an address characteristic of a location on the surface of the substrate and a value, the camera operative in capturing a first image of the substrate when the substrate is illuminated by the first light source and a second image of the substrate when the substrate is illuminated by the second light source; and a processor configured to calculate the difference between the pixel values in the first image and the second image on a pixel address by pixel address basis to form a third image; the processor configured to apply a threshold to the third image such that the third image comprises a plurality of pixels, the pixels having an address and a value, the value being either zero or above the threshold, the processor operative in counting the number of non-zero pixel values and causing the substrate to be rejected if the number of non-zero pixels exceeds a predetermined value; if the number of non-zero pixel values is below the predetermined value the processor being operative to record the addresses of the non-zero pixel values and operative to calculate a fourth image, the fourth image being the lesser of each pixel value between the first and second images for each pixel address, the processor operative in evaluating the pixel values in the fourth image at the recorded locations to determine the size and concentration of the pixel values and operative to reject the substrate if the size and concentration of the pixel values falls outside a predetermined tolerance.

22. An apparatus as in claim 21 wherein said first and second light sources are LED illuminators and the camera is a CMOS sensor.

23. An apparatus as in claim 21 wherein the processor is configured to apply gray scale morphology to the fourth image.

24. An apparatus as in claim 21 wherein the processor is further configured to calculate the difference between the pixel values in the first image and the second image on a pixel address by pixel address basis and to take an absolute value of the difference on a pixel address by pixel address basis to form the third image.

* * * * *